United States Patent
Pless (10) Patent No.: US 8,473,062 B2
(45) Date of Patent: Jun. 25, 2013

(54) METHOD AND DEVICE FOR THE TREATMENT OF HEADACHE

(75) Inventor: Benjamin David Pless, Atherton, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 372 days.

(21) Appl. No.: 12/434,457

(22) Filed: May 1, 2009

(65) Prior Publication Data

US 2009/0276005 A1 Nov. 5, 2009

Related U.S. Application Data

(60) Provisional application No. 61/126,173, filed on May 1, 2008.

(51) Int. Cl.
*A61N 1/00* (2006.01)
(52) U.S. Cl.
USPC ............................................. 607/46
(58) Field of Classification Search
USPC .............. 607/45; 600/377, 378, 46, 547, 548, 600/554
See application file for complete search history.

(56) References Cited

U.S. PATENT DOCUMENTS

| | | | |
|---|---|---|---|
| 2,123,980 A | 7/1938 | Warwick | |
| 2,182,071 A | 12/1939 | Crossley | |
| 3,357,434 A | 12/1967 | Abell | |
| 3,746,004 A | 7/1973 | Jankelson | |
| 3,862,321 A | 1/1975 | Adams et al. | |
| 3,914,283 A | 10/1975 | Okamoto et al. | |
| 3,923,060 A | 12/1975 | Ellinwood, Jr. | |
| 3,925,469 A | 12/1975 | Adams et al. | |
| 4,073,917 A | 2/1978 | Sandberg et al. | |
| 4,102,344 A | 7/1978 | Conway et al. | |
| 4,117,160 A | 9/1978 | Molnar et al. | |
| 4,147,804 A | 4/1979 | Diamond et al. | |
| 4,217,349 A | 8/1980 | Katsube et al. | |
| 4,298,603 A | 11/1981 | Chang et al. | |

(Continued)

FOREIGN PATENT DOCUMENTS

| EP | 69427 A2 | 1/1983 |
|---|---|---|
| EP | 0970813 A2 | 1/2000 |

(Continued)

OTHER PUBLICATIONS

Sinkj, Thomas, Apr. 2006, Electroneurography, Encyclopedia of Medical Devices and Instrumentation, Second Edition, p. 112.*

(Continued)

*Primary Examiner* — Christopher D Koharski
*Assistant Examiner* — Nadia Ahmad
(74) *Attorney, Agent, or Firm* — Shay Glenn LLP (57) ABSTRACT

A method is provided for the suppression or prevention of pain, movement disorders, epilepsy, cerebrovascular diseases, autoimmune diseases, sleep disorders, autonomic disorders, abnormal metabolic states, disorders of the muscular system, and neuropsychiatric disorders in a patient. The method comprises inserting an electrode into a patient. The electrode can be positioned on or proximate to a neural structure, and the electrode can detect an ENG signal. In some embodiments, the neural structure can be the patient's sphenopalatine ganglia ("SPG"), sphenopalatine nerves ("SPN"), or vidian nerves ("VN"). Placement of the electrode can be tested by detecting a characteristic ENG. If the characteristic ENG indicates that the electrode is not positioned on the target neural structure, the electrode can be repositioned.

11 Claims, 5 Drawing Sheets

U.S. PATENT DOCUMENTS

| | | |
|---|---|---|
| 4,305,402 A | 12/1981 | Katims |
| 4,352,820 A | 10/1982 | Scurlock et al. |
| 4,379,161 A | 4/1983 | Thominet et al. |
| 4,397,845 A | 8/1983 | Allen |
| 4,441,210 A | 4/1984 | Hochmair et al. |
| 4,495,174 A | 1/1985 | Allcock et al. |
| 4,519,400 A | 5/1985 | Brenman et al. |
| 4,529,601 A | 7/1985 | Broberg et al. |
| 4,550,733 A | 11/1985 | Liss et al. |
| 4,551,453 A | 11/1985 | Marsili |
| 4,565,200 A | 1/1986 | Cosman |
| 4,592,359 A | 6/1986 | Galbraith |
| 4,622,219 A | 11/1986 | Haynes |
| 4,627,438 A | 12/1986 | Liss et al. |
| 4,632,940 A | 12/1986 | Chiarino et al. |
| 4,646,744 A | 3/1987 | Capel |
| 4,692,147 A | 9/1987 | Duggan |
| 4,695,576 A | 9/1987 | af Ekenstam et al. |
| 4,718,423 A | 1/1988 | Willis et al. |
| 4,727,145 A | 2/1988 | Press |
| 4,776,349 A | 10/1988 | Nashef et al. |
| 4,784,142 A | 11/1988 | Liss et al. |
| 4,830,008 A | 5/1989 | Meer |
| 4,833,149 A | 5/1989 | Press |
| 4,856,526 A | 8/1989 | Liss et al. |
| 4,870,086 A | 9/1989 | Sandberg |
| 4,871,475 A | 10/1989 | Lubowitz et al. |
| 4,886,493 A | 12/1989 | Yee |
| 4,920,979 A | 5/1990 | Bullara |
| 4,937,078 A | 6/1990 | Mezei et al. |
| 4,976,711 A | 12/1990 | Parins et al. |
| 5,038,781 A | 8/1991 | Lynch |
| 5,085,868 A | 2/1992 | Mattsson et al. |
| 5,178,156 A | 1/1993 | Takishima et al. |
| 5,193,539 A | 3/1993 | Schulman et al. |
| 5,199,428 A | 4/1993 | Obel et al. |
| 5,215,086 A | 6/1993 | Terry, Jr. et al. |
| 5,227,165 A | 7/1993 | Domb et al. |
| 5,234,957 A | 8/1993 | Mantelle |
| 5,255,691 A | 10/1993 | Otten |
| 5,259,387 A | 11/1993 | dePinto |
| 5,314,458 A | 5/1994 | Najafi |
| 5,318,592 A | 6/1994 | Schaldach |
| 5,330,515 A | 7/1994 | Rutecki et al. |
| 5,335,657 A | 8/1994 | Terry, Jr. et al. |
| 5,344,438 A | 9/1994 | Testerman et al. |
| 5,360,805 A | 11/1994 | Ask et al. |
| 5,387,587 A | 2/1995 | Hausler et al. |
| 5,411,546 A | 5/1995 | Bowald et al. |
| 5,420,151 A | 5/1995 | Hammarberg et al. |
| 5,428,006 A | 6/1995 | Bechgaard et al. |
| 5,433,739 A | 7/1995 | Sluijter et al. |
| 5,458,626 A | 10/1995 | Krause |
| 5,458,631 A | 10/1995 | Xavier |
| 5,490,520 A | 2/1996 | Schaefer et al. |
| 5,514,131 A | 5/1996 | Edwards et al. |
| 5,540,730 A | 7/1996 | Terry, Jr. et al. |
| 5,540,734 A | 7/1996 | Zabara |
| 5,545,219 A | 8/1996 | Kuzma |
| 5,558,622 A | 9/1996 | Greenberg |
| 5,569,166 A | 10/1996 | Stone |
| 5,578,061 A | 11/1996 | Stroetmann et al. |
| 5,591,216 A | 1/1997 | Testerman et al. |
| 5,640,764 A | 6/1997 | Strojnik |
| 5,645,570 A | 7/1997 | Corbucci |
| 5,653,734 A | 8/1997 | Alt |
| 5,658,318 A | 8/1997 | Stroetmann et al. |
| 5,660,837 A | 8/1997 | Lundquist |
| 5,676,955 A | 10/1997 | Ansmann et al. |
| 5,700,282 A | 12/1997 | Zabara |
| 5,707,400 A | 1/1998 | Terry, Jr. et al. |
| 5,711,316 A | 1/1998 | Elsberry et al. |
| 5,713,922 A | 2/1998 | King |
| 5,735,817 A | 4/1998 | Shantha |
| 5,756,520 A | 5/1998 | Ask et al. |
| 5,766,605 A | 6/1998 | Sanders et al. |
| 5,824,027 A | 10/1998 | Hoffer et al. |
| 5,843,021 A | 12/1998 | Edwards et al. |
| 5,861,014 A | 1/1999 | Familoni |
| 5,865,843 A | 2/1999 | Baudino |
| 5,938,688 A | 8/1999 | Schiff |
| 6,001,088 A | 12/1999 | Roberts et al. |
| 6,006,134 A | 12/1999 | Hill et al. |
| 6,016,449 A | 1/2000 | Fischell et al. |
| 6,026,326 A | 2/2000 | Bardy |
| 6,058,331 A | 5/2000 | King |
| 6,073,048 A | 6/2000 | Kieval et al. |
| 6,093,145 A | 7/2000 | Vom Berg et al. |
| 6,094,598 A | 7/2000 | Elsberry et al. |
| 6,104,957 A | 8/2000 | Alo et al. |
| 6,128,538 A | 10/2000 | Fischell et al. |
| 6,132,384 A | 10/2000 | Christopherson et al. |
| 6,134,474 A | 10/2000 | Fischell et al. |
| 6,141,590 A | 10/2000 | Renirie et al. |
| 6,146,380 A | 11/2000 | Racz et al. |
| 6,161,044 A | 12/2000 | Silverstone |
| 6,161,048 A | 12/2000 | Sluijter et al. |
| 6,178,349 B1 | 1/2001 | Kieval |
| 6,205,359 B1 | 3/2001 | Boveja |
| 6,246,912 B1 | 6/2001 | Sluijter et al. |
| 6,251,126 B1 | 6/2001 | Ottenhoff et al. |
| 6,259,952 B1 | 7/2001 | Sluijter et al. |
| 6,262,377 B1 | 7/2001 | Nielsen et al. |
| 6,269,270 B1 | 7/2001 | Boveja |
| 6,292,695 B1 | 9/2001 | Webster, Jr. et al. |
| 6,308,105 B1 | 10/2001 | Duysens et al. |
| 6,353,792 B1 | 3/2002 | Murthy |
| 6,356,786 B1 | 3/2002 | Rezai et al. |
| 6,356,787 B1 | 3/2002 | Rezai et al. |
| 6,356,788 B2 | 3/2002 | Boveja |
| 6,366,814 B1 | 4/2002 | Boveja et al. |
| 6,400,982 B2 | 6/2002 | Sweeney et al. |
| 6,405,079 B1 | 6/2002 | Ansarinia |
| 6,432,986 B2 | 8/2002 | Levin |
| 6,438,423 B1 | 8/2002 | Rezai et al. |
| 6,456,786 B1 | 9/2002 | Uchida et al. |
| 6,458,157 B1 | 10/2002 | Suaning |
| 6,491,940 B1 | 12/2002 | Levin |
| 6,511,500 B1 | 1/2003 | Rahme |
| 6,526,318 B1 | 2/2003 | Ansarinia |
| 6,564,096 B2 | 5/2003 | Mest |
| 6,564,102 B1 | 5/2003 | Boveja |
| 6,610,713 B2 | 8/2003 | Tracey |
| 6,615,081 B1 | 9/2003 | Boveja |
| 6,633,779 B1 | 10/2003 | Schuler |
| 6,647,296 B2 | 11/2003 | Fischell et al. |
| 6,665,562 B2 | 12/2003 | Gluckman et al. |
| 6,668,191 B1 | 12/2003 | Boveja |
| 6,735,475 B1 | 5/2004 | Whitehurst et al. |
| 6,760,626 B1 | 7/2004 | Boveja |
| 6,788,975 B1 | 9/2004 | Whitehurst et al. |
| RE38,654 E | 11/2004 | Hill et al. |
| 6,819,956 B2 * | 11/2004 | DiLorenzo ............ 607/45 |
| 6,853,858 B2 | 2/2005 | Shalev |
| 6,885,888 B2 | 4/2005 | Rezai |
| 6,978,180 B2 | 12/2005 | Tadlock |
| 7,003,352 B1 | 2/2006 | Whitehurst |
| 7,027,860 B2 | 4/2006 | Bruninga et al. |
| 7,047,078 B2 * | 5/2006 | Boggs et al. ............ 607/41 |
| 7,076,307 B2 | 7/2006 | Boveja et al. |
| 7,113,033 B2 | 9/2006 | Barnett |
| 7,117,033 B2 | 10/2006 | Shalev et al. |
| 7,120,489 B2 | 10/2006 | Shalev et al. |
| 7,149,574 B2 | 12/2006 | Yun et al. |
| 7,167,751 B1 | 1/2007 | Whitehurst et al. |
| 7,191,012 B2 | 3/2007 | Boveja et al. |
| 7,203,548 B2 | 4/2007 | Whitehurst et al. |
| 7,209,787 B2 | 4/2007 | DiLorenzo |
| 7,277,758 B2 | 10/2007 | DiLorenzo |
| 7,285,118 B1 | 10/2007 | Lozano |
| 7,286,879 B2 | 10/2007 | Wallace |
| 7,292,890 B2 | 11/2007 | Whitehurst et al. |
| 7,308,302 B1 | 12/2007 | Schuler et al. |
| 7,340,298 B1 | 3/2008 | Barbut |
| 7,349,743 B2 | 3/2008 | Tadlock |
| 7,363,076 B2 | 4/2008 | Yun et al. |
| 7,369,897 B2 | 5/2008 | Boveja et al. |

| | | |
|---|---|---|
| 7,403,821 B2 * | 7/2008 | Haugland et al. ............... 607/49 |
| 7,477,945 B2 | 1/2009 | Rezia et al. |
| 7,494,458 B2 | 2/2009 | Fischell et al. |
| 7,532,938 B2 | 5/2009 | Machado et al. |
| 7,561,919 B2 | 7/2009 | Shalev et al. |
| 7,623,924 B2 | 11/2009 | Narciso, Jr. |
| 7,640,057 B2 * | 12/2009 | Libbus et al. ...................... 607/2 |
| 7,689,276 B2 | 3/2010 | Dobak |
| 7,763,034 B2 | 7/2010 | Siegel et al. |
| 7,848,816 B1 | 12/2010 | Wenzel et al. |
| 2002/0026222 A1 | 2/2002 | Schauerte et al. |
| 2002/0073334 A1 | 6/2002 | Sherman et al. |
| 2002/0107553 A1 | 8/2002 | Hill et al. |
| 2002/0169365 A1 | 11/2002 | Nakada et al. |
| 2003/0004549 A1 | 1/2003 | Hill et al. |
| 2003/0018367 A1 | 1/2003 | DiLorenzo |
| 2003/0018368 A1 * | 1/2003 | Ansarinia ........................ 607/46 |
| 2003/0060857 A1 | 3/2003 | Perrson et al. |
| 2003/0065374 A1 | 4/2003 | Honeck |
| 2003/0100924 A1 | 5/2003 | Foreman et al. |
| 2003/0133877 A1 | 7/2003 | Levin |
| 2003/0144709 A1 | 7/2003 | Zabara et al. |
| 2003/0176898 A1 | 9/2003 | Gross et al. |
| 2003/0181951 A1 | 9/2003 | Cates |
| 2003/0181958 A1 | 9/2003 | Dobak, III |
| 2003/0181959 A1 | 9/2003 | Dobak, III |
| 2003/0212440 A1 | 11/2003 | Boveja |
| 2003/0216792 A1 | 11/2003 | Levin et al. |
| 2004/0015204 A1 | 1/2004 | Whitehurst et al. |
| 2004/0019364 A1 | 1/2004 | Kieval et al. |
| 2004/0049235 A1 | 3/2004 | Deno et al. |
| 2004/0172084 A1 | 9/2004 | Knudson et al. |
| 2004/0210295 A1 | 10/2004 | Brushey |
| 2004/0230255 A1 | 11/2004 | Dobak, III |
| 2004/0236381 A1 | 11/2004 | Dinsmoor et al. |
| 2005/0065562 A1 | 3/2005 | Rezai |
| 2005/0065573 A1 | 3/2005 | Rezai |
| 2005/0075701 A1 | 4/2005 | Shafer |
| 2005/0075702 A1 | 4/2005 | Shafer |
| 2005/0102006 A1 | 5/2005 | Whitehurst et al. |
| 2005/0143787 A1 | 6/2005 | Boveja et al. |
| 2005/0149156 A1 | 7/2005 | Libbus et al. |
| 2005/0153885 A1 | 7/2005 | Yun et al. |
| 2005/0154419 A1 | 7/2005 | Whitehurst et al. |
| 2005/0154426 A1 | 7/2005 | Boveja et al. |
| 2005/0159790 A1 | 7/2005 | Shalev |
| 2005/0197675 A1 | 9/2005 | David et al. |
| 2005/0209654 A1 | 9/2005 | Boveja et al. |
| 2005/0216070 A1 | 9/2005 | Boveja et al. |
| 2005/0234523 A1 | 10/2005 | Levin et al. |
| 2005/0281751 A1 | 12/2005 | Levin |
| 2006/0004423 A1 | 1/2006 | Boveja et al. |
| 2006/0020299 A1 | 1/2006 | Shalev |
| 2006/0064140 A1 | 3/2006 | Whitehurst et al. |
| 2006/0074450 A1 | 4/2006 | Boveja et al. |
| 2006/0074463 A1 | 4/2006 | Seeberger et al. |
| 2006/0079945 A1 | 4/2006 | Libbus |
| 2006/0085046 A1 | 4/2006 | Rezai et al. |
| 2006/0095088 A1 | 5/2006 | De Ridder |
| 2006/0100667 A1 | 5/2006 | Machado et al. |
| 2006/0100668 A1 | 5/2006 | Ben-David et al. |
| 2006/0100671 A1 | 5/2006 | De Ridder |
| 2006/0111754 A1 | 5/2006 | Rezai |
| 2006/0116721 A1 | 6/2006 | Yun et al. |
| 2006/0149337 A1 | 7/2006 | John |
| 2006/0167497 A1 | 7/2006 | Armstrong et al. |
| 2006/0173495 A1 | 8/2006 | Armstrong et al. |
| 2006/0184211 A1 | 8/2006 | Gaunt et al. |
| 2006/0195169 A1 | 8/2006 | Gross |
| 2006/0206165 A1 | 9/2006 | Jaax et al. |
| 2006/0235484 A1 | 10/2006 | Jaax et al. |
| 2006/0287678 A1 | 12/2006 | Shafer |
| 2006/0293723 A1 | 12/2006 | Whitehurst et al. |
| 2007/0021801 A1 | 1/2007 | Heruth et al. |
| 2007/0021802 A1 | 1/2007 | Heruth et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027498 A1 | 2/2007 | Maschino et al. |
| 2007/0039625 A1 | 2/2007 | Heruth et al. |
| 2007/0049988 A1 | 3/2007 | Carbunaru et al. |
| 2007/0066997 A1 | 3/2007 | He et al. |
| 2007/0067004 A1 | 3/2007 | Boveja et al. |
| 2007/0083245 A1 | 4/2007 | Lamensdorf et al. |
| 2007/0100411 A1 | 5/2007 | Bonde |
| 2007/0106143 A1 | 5/2007 | Flaherty |
| 2007/0112404 A1 | 5/2007 | Mann et al. |
| 2007/0156177 A1 | 7/2007 | Harel et al. |
| 2007/0156179 A1 | 7/2007 | Karashurov |
| 2007/0167984 A1 | 7/2007 | Kieval et al. |
| 2007/0203521 A1 | 8/2007 | Dobak et al. |
| 2007/0233193 A1 | 10/2007 | Craig |
| 2007/0250119 A1 | 10/2007 | Tyler et al. |
| 2007/0250145 A1 * | 10/2007 | Kraus et al. ................... 607/136 |
| 2007/0255368 A1 | 11/2007 | Bonde et al. |
| 2007/0255369 A1 | 11/2007 | Bonde et al. |
| 2007/0293906 A1 | 12/2007 | Cowan et al. |
| 2008/0027346 A1 | 1/2008 | Litt et al. |
| 2008/0033509 A1 | 2/2008 | Shalev et al. |
| 2008/0046053 A1 | 2/2008 | Wagner et al. |
| 2008/0071318 A1 * | 3/2008 | Brooke et al. .................. 607/28 |
| 2008/0086182 A1 | 4/2008 | Ben-David et al. |
| 2008/0103547 A1 | 5/2008 | Okun et al. |
| 2008/0103569 A1 | 5/2008 | Gerber |
| 2008/0132933 A1 | 6/2008 | Gerber |
| 2008/0132981 A1 | 6/2008 | Gerber |
| 2008/0132982 A1 | 6/2008 | Gerber |
| 2008/0140000 A1 | 6/2008 | Shuros et al. |
| 2008/0161877 A1 * | 7/2008 | Kirby et al. ...................... 607/42 |
| 2008/0161894 A1 | 7/2008 | Ben-David et al. |
| 2008/0183237 A1 | 7/2008 | Errico et al. |
| 2008/0183246 A1 | 7/2008 | Patel et al. |
| 2008/0183253 A1 | 7/2008 | Bly |
| 2008/0262566 A1 | 10/2008 | Jaax |
| 2008/0269716 A1 | 10/2008 | Bonde et al. |
| 2009/0012577 A1 | 1/2009 | Rezai et al. |
| 2009/0036949 A1 * | 2/2009 | Kokones et al. ................ 607/45 |
| 2009/0105783 A1 | 4/2009 | Solberg et al. |
| 2009/0118780 A1 | 5/2009 | DiLorenzo |
| 2009/0216287 A1 | 8/2009 | Ansarinia |
| 2009/0254147 A1 | 10/2009 | Ansarinia |
| 2009/0264956 A1 * | 10/2009 | Rise et al. ....................... 607/45 |
| 2009/0276025 A1 | 11/2009 | Burnes et al. |
| 2009/0312817 A1 | 12/2009 | Hogle et al. |
| 2009/0320845 A1 | 12/2009 | Fishman et al. |
| 2010/0185258 A1 | 7/2010 | Papay |
| 2010/0268306 A1 | 10/2010 | Maniak et al. |
| 2011/0029037 A1 | 2/2011 | Rezai et al. |

FOREIGN PATENT DOCUMENTS

| | | |
|---|---|---|
| EP | 754060 B1 | 3/2003 |
| RU | 2108817 C1 | 4/1996 |
| WO | WO85/00599 A1 | 2/1985 |
| WO | WO92/07605 A1 | 5/1992 |
| WO | WO95/21821 A1 | 2/1994 |
| WO | WO97/02000 A1 | 1/1997 |
| WO | WO97/15548 A1 | 5/1997 |
| WO | WO97/23467 A1 | 7/1997 |
| WO | WO97/38675 A1 | 10/1997 |
| WO | WO01/85094 A2 | 11/2001 |
| WO | WO01/97905 A1 | 12/2001 |
| WO | WO03/082123 A2 | 10/2003 |
| WO | WO2005/105202 A1 | 11/2005 |

OTHER PUBLICATIONS

Rao, K. Pampapathi, Oct. 11, 2004, Effectivenss of temporal pattern in the input to a ganglion, Journal of Neurobiology, vol. 1, Issue 2, pp. 233-245 (abstract).*

Alstadhaug, K.B.; Migraine and the hypothalamus; Cephalalgia (Blackwell Publishing Ltd.); pp. 1-9; 2009.

Boysen et al.; Parasympathetic tonic dilatory influences on cerebral vessels; Autonomic Neuroscience: Basic and Clinical; vol. 147; pp. 101-104; 2009.

Cohen et al.; Sphenopalatine ganglion block for postdural puncture headache; Anaesthesia; vol. 64; pp. 574-575; 2009.

Iliff et al.; Epoxyeicosanoids as mediators of neurogenic vasodilation in cerebral vessels; Am J Physiol Heart Circ Physiol; vol. 296; pp. 1352-1363; Mar. 20, 2009.
Kosaras et al.; Sensory innervation of the calvarial bones of the mouse; The Journal of Comparative Neurology (John Wiley & Sons); 48 pgs.; 2009.
Narouze et al.; Sphenopalatine ganglion radiofrequency ablation for the management of chronic cluster headache; Headache; vol. 49; pp. 571-577; Apr. 2009.
Narouze et al.; Sphenopalatine ganglion stimulation for the acute treatment of intractable migraine; American Academy of Pain Medicine Annual Meeting Abstracts; pp. 226 (Abstract No. 157); 2009.
Scott et al.; Trigger point injections for chronic non-malignant musculoskeletal pain: a systematic review; Pain Medicine; vol. 10; No. 1; pp. 54-69; 2009.
Toda et al.; Cerebral blood flow regulation by nitric oxide: recent advances; Pharmacol Rev; vol. 61; No. 1; pp. 62-97; 2009.
Vitek; Mechanisms of deep brain stimulation: excitation or inhibition; Movement Disorders; vol. 17; supp. 3; pp. S69-S72; 2002.
Zarembinski et al.; Sphenopalatine ganglion block in traumatic trigeminal neuralgia and the outcome to radiosurgical ablation; American Academy of Pain Medicine Annual Meeting Abstracts; pp. 200 (abstract No. 102); 2009.
Pless et al.; U.S. Appl. No. 12/649,119 entitled "Integrated Delivery and Visualization Tool for a Neuromodulation System," filed Dec. 29, 2009.
Levin, Bruce; U.S. Appl. No. 12/683,301 entitled "Method for Directed Intranasal Administration of a Composition," filed Jan. 6, 2010.
Fletcher et al.; U.S. Appl. No. 12/688,524 entitled "Approval Per Use Implanted Neurostimulator," filed Jan. 15, 2010.
Wingeier et al.; U.S. Appl. No. 12/692,444 entitled "Method and Devices for Adrenal Stimulation," filed Jan. 22, 2010.
Ardell et al.; "Differential sympathetic regulation of automatic, conductile, and contractile tissue in dog heart;" American Physiological Society; pp. H1050-H1059; Jun. 6, 1988.
Babe, "Treatment of sphenopalatine ganglion neuralgia", An Otorrinolaringol Ibero Am, vol. 16(5): 463-74 (1989) (abstract).
Barre, "Cocaine as an abortive agent in cluster headache", Headache, vol. 22: 69-73 (1982).
Benumof et al.; Pulmonary artery catheterization; In Clinical Procedures in Anesthesia and Intensive Care; JB Lippincott Company; pp. 405-441; 1992.
Berger et al., "Does topical anesthesia of the sphenopalatine ganglion with cocaine or lidocaine relieve low back pain?", Anesth Analg, vol. 35: 87-108 (1925).
Brooksby et al.; Dynamic changes in splanchnic blood flow and blood volume in dogs during activation of sympathetic nerves; Circulation Research; vol. 29; pp. 227-238; 1971.
Brooksby et al; Release of blood from the splanchnic circulation in dogs; Circulation Research; vol. 31; pp. 105-118; 1972.
Browne et al., "Concurrent cervical and craniofacial pain" Oral Surg Oral Med Oral Path 86(6): 633-640 (Dec. 1998).
Carneiro et al.; Blood reservoir function of dog spleen, liver and intestine; American Journal of Physiology; vol. 232; No. 1; pp. H67-H72; 1977.
Carroll et al., "Motor cortex stimulation for chronic neuropathic pain: a preliminary study of 10 cases" Pain 84:431-437 (2000).
Cepero et al., "Long-term results of sphenopalatine ganglioneurectomy for facial pain", Am J Otolaryngol, 8(3): 171-4 (1987).
Cheatham et al.; Shock: An overview, surgical critical care service; Department of Surgical Education; Orlando Regional Medical Center; 5th ed.; pp. 1-40; 2003.
Cook, "Cryosurgery of headache", Res Clin Stud Headache, vol. 5: 86-101 (1978) (abstract).
Cooper et al.; Neural effects on sinus rate and atrioventricular conduction produced by electrical stimulation from a transvenous electrode catheter in the canine right pulmonary artery; Circulation Research; vol. 46; pp. 48-57; 1980.
Cutrer et al., "Effects of PNU-109,291, a selective 5H-T1D receptor agonist, on electrically induced dural plasma extravasation and capsaicin-evoked c-fos immunoreactivity within trigeminal nucleus caudalis" Neuropharm 38:1043-1053 (1999).
Delepine et al., "Plasma protein extravasation induced in the rat dura mater by stimulation of the parasympathetic sphenopalatine ganglion", Exp Neurology, vol. 147: 389-400 (1997).
Devoghel, "Cluster headache and sphenopalatine block", Acta Anaesthesio Belg, vol. 32(1), pp. 101-107 (1981).
Feindel et al., "The tentorial nerves and localization of intracranial pain in man" Neurology 555-563 (1955).
Ferrante et al., "Sphenopalatine ganglion block for the treatment of myofascial pain of the head, neck, and shoulders", Reg Anesth Pain, vol. 23(1): 30-6 (1998) (abstract).
Frisardi et al., "Electric versus magnetic transcranial stimulation of the trigeminal system in healthy subjects. Clinical applications in gnathology.", J Oral Rehabil, 24(12): 920-8 (1986) (abstract).
Goadsby et al., "Differential effects of low dose CP122,288 and eletriptan on Fos expression due to stimulation of the superior sagittal sinus in cat" Pain 82:15-22 (1999).
Goadsby et al., "Stimulation of an intracranial trigeminally-innervated structure selectively increases cerebral blood flow" Brain Research 751:247-252 (1997).
Goadsby et al., "Substance P blockade with the potent and centrally acting antagonist GR205171 does not effect central trigeminal activity with superior sagittal sinus stimuation" Neuroscience 86(1):337-343 (1998).
Goadsby et al., "The trigeminovascular system and migraine: studies characterizing cerebrovascular and neuropeptide changes seen in humans and cats" Ann Neurol 33:48-56 (1993).
Goadsby et al., Effect of stimulation of trigeminal ganglion on regional cerebral blood flow in cats; Am J. Physiol.; vol. 22; pp. R270-R274; 1987.
Goadsby, "Sphenopalatine ganglion stimulation increases regional blood flow independent of glucose utilization in the cat", Brain Research, vol. 506: 145-8 (1990).
Gregoire, "Cluster headaches", Can Nurse, vol. 87(9): 33-5 (1991) (abstract).
Hardebo, Jan-Erik; Activation of pain fibers to the internal carotid artery intracranially may cause the pain and local signs of reduced sympathetic and enhanced parasympathetic activity in cluster headache; Headache; 31; pp. 314-320; May 1991.
Hardebo, Jan-Erik; On pain mechanisms in cluster headache; Headache; 31; pp. 91-106; 1991.
Headache Classification Committee of the International Headache Society, "Classification and diagnostic criteria for headache disorders, cranial neuralgias and facial pain", Cephalalgia, Supp & 0:13, 19-24 and 35-38 (1988).
Heusch et al.; Adrenergic mechanisms in myocardial ischemia; Supp. to Basic Research in Cardiology; vol. 85; 1990.
Hillier; Monitored anesthesia care; Clinical Anesthesia; Ch. 47; pp. 1239-1254; 2001.
Hoskin et al., "Fos expression in the trigeminocervical complex of the cat after stimulation of superior sagittal sinus is reduced by L-NAME" Neuroscience Letters 266:173-176 (1999).
Hudson; Basic principles of clinical pharmacology; Clinical Anesthesia; Ch. 11; pp. 239-260; 2001.
Ibarra, Eduardo; Neuromodulación del Ganglio Esfenopalation para Aliviar los Sintomas del la Cefalea en Raciomos; Boletin El Dolor; vol. 46, No. 16; pp. 12-18; 2007 (with English translation).
Janes et al.; Anatomy of human extrinsic cardiac nerves and ganglia; American Journal of Cardiology; vol. 57; pp. 299-309; 1986.
Janzen et al., "Sphenopalatine blocks in the treatment of pain in fibromyalgia and myofascial pain syndrome", Laryngoscope, vol. 107(10):1420-2 (1997).
Kittrelle et al., "Cluster headache. Local anesthetic abortive agents", Arch Neurol, vol. 42(5): 496-8 (May 1985).
Kudrow et al., "Rapid and sustained relief of migraine attacks with intranasal lidocaine: preliminary findings", Headache, vol. 25: 79-82 (1995).
Kudrow, "Natural history of cluster headaches—part 1 outcome of drop-out patients", Headache, vol. 22: 203-6 (1982).
Kushiku et al.; Upregulation of Immunoreactive Angiotensin II Release and Angiotensinogen mRNA Expression by High-Frequency Preganglionic Stimulation at the Canine Cardiac Sympathetic Ganglia; Circ Res.; 88; pp. 110-116; 2001.

Lambert et al.; Comparative effects of stimulation of the trigeminal ganglion and the superior sagittal sinus on cerebral blood flow and evoked potentials in the cat; Brain Research; vol. 453; pp. 143-149; 1988.

Lebovits et al., "Sphenopalatine ganglion block: clinical use in the pain management clinic", Clin J Pain, vol. 6(2): 131-6 (1990).

Levine et al.; Central venous and pulmonary artery catheter monitoring; Critical Care Monitoring from Pre-Hospital to the ICU; pp. 145-158.

Maizels et al., "Intranasal lidocaine for treatment of migraine", JAMA, vol. 276 (4): 319-21 (1996).

Manahan et al., "Sphenopalatine ganglion block relieves symptoms of trigeminal neuralgia: a case report", Nebr Med J, vol. 81(9): 306-9 (1996) (abstract).

Matsumoto et al.; Effective sites by sympathetic beta-andrenergic and vagal nonadrenergic inhibitory stimulation in constricted airways; Am Rev Respir Dis; vol. 132; pp. 1113-1117; Nov. 1985.

Matthey et al.; Bedside catheterization of the pulmonary artery: risks compared with benefits; In Clinical Procedures in Anesthesia and Intensive Care; JB Lippincott Company; vol. 109; pp. 826-834; 1988.

Meyer et al., "Sphenopalatine ganglionectomy for cluster headache", Arch Otolaryngol, vol. 92(5): 475-84 (Nov. 1970).

Meyerson et al.; Alleviation of Atypical trigeminal pain by stimulation of the gasserian ganglion via an implanted electrode; Acta Neurochirurgica; supp. 30; pp. 303-309; 1980.

Moskowitz et al., "Basic mechanisms in vascular headache" Headache 8 (4):801-815 (Nov. 1990).

Moskowitz, Michael; Cluster headache: evidence for a pathophysiologic focus in the superior pericarotid cavernous sinus plexus; Headache; vol. 28; pp. 584-586; 1988.

Murphy et al.; Human cardiac nerve stimulation; The Annals of Thoracic Surgery; vol. 54; p. 502; 1992.

Nguyen et al., "Chronic motor cortex stimulation in the treatment of central and neuropathic pain. Correlations between clinical, electrophysiological and anatomical data" Pain 82:245-251 (1999).

Onofrio et al., "Surgical treatment of chronic cluster headache", Mayo Clin Proc, vol. 61(7), pp. 537-544 (1986).

Peterson et al., "Sphenopalatine ganglion block: a safe and easy method for the management of orofacial pain", Cranio, vol. 13(3): 177-81 (1995) (abstract).

Phebus et al., "The non-peptide NK-1 receptor antagonist LY303870 inhibits neurogenic dural inflammation in guinea pigs" Life Sciences 60(18):1553-1561 (1997).

Pollock et al., "Stereotactic radiosurgical treatment of sphenopalatine neuralgia", J Neurosurg, vol. 87(3): 450-3 (1997).

Reder et al., "Sphenopalatine ganglion block in treatment of acute and chronic pain", Diagnosis and treatment of chronic pain, John Wright, publisher, 97-108 (1982).

Reuter et al.; Experimental models of migraine; Funct Neurol; suppl. 15; pp. 9-18; 2000.

Ruskin, "Contributions to the study of the sphenopalatine ganglion", Laryngoscope, vol. 35(2): 87-108 (1925).

Ruskin; Sphenopalatine (nasal) gaglion: remote effects including "psychosomatic" symptons, rage reaction, pain, and spasm; Arch Phys Med Rehabil; vol. 60; pp. 353-359; Aug. 1979.

Ryan et al., "Sphenopalatine ganglion neuralgia and cluster headache: comparisons, contrasts, and treatment", Headache, vol. 17: 7-8 (1977).

Saade et al., "Patient-administered sphenopalatine ganglion block", Reg Anesth, vol. 21(1): 68-70 (1996) (abstract).

Sanders et al., "Efficacy of sphenopalatine ganglion blockade in 66 patients suffering from cluster headache: a 12- to 70-month follow-up evaluation", J Neurosurg., vol. 87(6), pp. 876-880 (Dec. 1997).

Scherlag et al.; Endovascular stimulation within the left pulmonary artery to induce slowing of heart rate and paroxysmal atrial fibrillation; Cardiovascular Research; vol. 54; pp. 470-475; 2002.

Schulz et al., "Localization of epileptic auras induced on stimulation by subdural electrodes" Epilepsia 38(12) 1321-1329 (1997).

Seylaz et al., "Effect of stimulation of the sphenopalatine ganglion on cortical blood flow in the rat", J Cerebr Blood Flow and Metab, vol. 8: 875-8 (1988).

Shuster et al., "Treatment of vasomotor rhinitis, trigeminal neuralgia and Sluder's syndrome by irradiation of the sphenopalatine ganglion with helium-neon lasers", Vestin Otorinolaringol, vol. 4: 35-40 (1988).

Sluder, "The syndrome of sphenopalatine ganglion neuralgia", Am J Medicament Sci, vol. 111: 868-878 (1910).

Sluder; The anatomical and clinical relations of the sphenopalatine (Meckel's) ganglion to the nose and its accessory sinuses; NY Med. J.; vol. 90; pp. 293-298; Aug. 1909.

Steude; Percutaneous electro stimulation of the trigeminal nerve in patients with atypical trigeminal neuralgia; Neurochirurgia; vol. 21; pp. 66-69; 1978.

Storer et al., "Microiontophoretic application of serotonin (5HT) 1B/1D agonists inhibits trigeminal cell firing in the cat" Brain 120:2171-2177 (1997).

Strassman et al., "Sensitization of meningeal sensory neurons and the origin of headaches" Nature 384:560-563 (Dec. 1996).

Suzuki et al., "Selective electrical stimulation of postganglionic cerebrovascular parasympathetic nerve fibers originating from the sphenopalatine ganglion enhances cortical blood flow in the rat", J Cerebr Blood Flow and Metab, vol. 10: 383-391 (1990).

Suzuki et al.; Trigeminal fibre collaterals storing substance P and calcitonin gene-related peptide ; Neuroscience; vol. 30; No. 3; pp. 595-604; 1989.

Taub et al., "Chronic electrical stimulation of the gasserian ganglion for the relief of pain in a series of 34 patients", J Neurosurg, vol. 86: 197-202 (1997).

Thalamic Stimulation and Trigeminal Neuralgia; Neuroscience Pathways (Publication of the Cleveland Clinic Foundation); Spring 1998 newsletter; pp. 1-2.

Walters et al.; Cerebrovascular projections from the sphenopalatine and otic ganglia to the middle cerebral artery of the cat; Stroke; vol. 17; pp. 488-494; 1986.

Young, "Electrical stimulation of the trigeminal nerve root for the treatment of chronic facial pain", J Neurosurg, vol. 83: 72-78 (1995).

Boling et al.; U.S. Appl. No. 12/765,712 entitled "Implantable Neurostimulator with Integral Hermetic Electronic Enclosure, Circuit Substrate, Monolithic Feed-Through, Lead Assembly and Anchoring Mechanism," filed Apr. 22, 2010.

Moskowitz; Neurogenic inflammation in the pathophysiology and treatment of migraine; Neurology; vol. 43; suppl. 3; pp. S16-S20; 1993.

- 443 Wingeier et al.; U.S. Appl. No. 12/791,690 entitled "Methods and Devices for Adrenal Stimulation," filed Jun. 1, 2010.

Gromova et al.; Sinusoidal modulated currents in comprehensive treatment of children with bronchial asthma; Voprosy Kurortologii Fizioterapii, I Lechebnoi Fizicheskoi Kultury; May-Jun; (3); pp. 45-47; 1981 (w/ English Abstract).

Guo et al.; Treatment of primary trigeminal neuralgia with acupuncture at the sphenopalatine ganglion; Journal of traditional chinese medicine; vol. 15(1) pp. 31-33; 1995.

Karashurov et al.; Radio frequency electrostimulation of the gangliated cord of the sympathetic nerve in patients with bronchial asthma; Surgery (Khigurgiia); vol. 1; pp. 44-46; 2000 (w/ English Abstract).

Karavis, "The neurophysiology of acupuncture: a viewpoint", Acupuncture in Medicine, vol. 15(1): 33-42 (May 1997).

* cited by examiner

METHOD AND DEVICE FOR THE TREATMENT OF HEADACHE

CROSS REFERENCE TO RELATED APPLICATIONS

This application claims the benefit under 35 U.S.C. 119 of U.S. Provisional Patent Application No. 61/126,173, filed May 1, 2008, titled "Method and Device for the Treatment of Headache." This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention is in the field of medical procedures and devices. More particularly, the present invention is in the field of medical procedures and devices that relate to treatment of a neural structure in the head such as the sphenopalatine ganglion, trigeminal ganglion, or vidian nerve.

BACKGROUND OF THE INVENTION

Headaches are one of the most common ailments, and afflict millions of individuals. The specific etiology of headaches may be difficult to pinpoint. Known sources of headache pain include trauma and vascular, neurovascular, autoimmune, degenerative, infectious, drug and medication-induced, inflammatory (sarcoid), neoplastic (primary or metastatic), metabolic-endocrine, iatrogenic (such as post-surgical), muscloskeletal and myofascial causes. Even if the condition underlying the headache pain is identified and treated, headache pain may persist.

Headaches have traditionally been treated with medications to prevent their recurrence and to alleviate acute pain and associated symptoms, such as nausea and vomiting. Non-invasive modalities of migraine treatment, which may be used alone or in combination, have included: diet modification, which may include the avoidance of known headache triggers (such as certain foods); biofeedback and relaxation techniques as well as other psychological modalities; acupuncture; chiropractic manipulation; and physical therapy. Anesthetic agents (such as Lidocaine) have been applied to the sphenopalatine ganglia, either directly, using a syringe, or indirectly, by soaking a long cotton swab in the anesthetic and placing the swab intranasally adjacent to the sphenopalatine ganglia, such that the anesthetic diffuses through the nasal mucosa to affect the sphenopalatine ganglia. Invasive approaches for the treatment of cluster headaches have included localized anesthetic block, surgical resection, radiofrequency, alcohol/phenol infiltration, radiosurgery and cryotherapy of the sphenopalatine ganglia and the trigeminal nerve and ganglion.

Newer techniques for treating a variety of neurological disorders have included electrical stimulation of cranial nerves of the central nervous system, such as the sphenopalatine ganglion, glossopharangeal, vagus, or trigeminal nerves. The principle behind these approaches is to disrupt or modulate abnormal neuronal transmissions in the nervous system through the application of the modulating electrical signals. However, surgical implantation of neurostimulator electrodes on or proximate a target cranial nerve can be difficult and typically relies on patient response to electrical stimulation (i.e., reporting of tingling, buzzing, vibratory sensation or pain) to determine which cranial nerve the implant is positioned on.

Thus, there is a need in the implantable medical devices field for a method of accurately positioning a neurostimulator electrode on a cranial nerve of the central nervous system, including the nerves of the sphenopalatine ganglion, maxillary nerve, and vidian nerve. Such improvements may significantly increase implantation accuracy and success rates, and reduce surgical implantation time and patient discomfort.

SUMMARY OF THE INVENTION

Generally, the present invention contemplates the use of an implantable neurostimulator for treatment of medical ailments such as headache.

In one embodiment, method of positioning an electrode on or proximate to at least one of a patient's sphenopalatine ganglia, sphenopalatine nerves, or vidian nerves is provided, the method comprising inserting an electrode into the patient, detecting an ENG with the electrode, and testing placement of the electrode by detecting a characteristic ENG. The method can further comprise activating the electrode to apply an electrical signal to at least one of the sphenopalatine ganglia, sphenopalatine nerves, or vidian nerves.

In some embodiments, the method can further comprise repositioning the electrode after the testing step. In other embodiments, the method can comprise repositioning the electrode if the characteristic ENG is not detected. If a characteristic ENG is not detected, the detecting and testing steps can be repeated.

In some embodiments, the characteristic ENG is a time domain profile. The characteristic ENG can also be a frequency profile, an amplitude characteristic, a bursting pattern, a spikes pattern, or other similar characteristic ENG signals.

In some embodiments, the electrode can be a needle electrode. In other embodiments, the electrode can be a micro-electrode, a macro-electrode, or other similar structures.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Methods and medical devices are provided to deliver treatment by stimulation of a neural structure in the head. The medical device is typically an implantable neurostimulator that delivers electrical stimulation to or near a neural structure with an electrode. In some embodiments, the electrode can be positioned on a probe assembly and configured to deliver electrical stimulation and monitor an electroneurogram (ENG). In particular, these methods and devices may be adapted for use in the treatment of autonomic disorders such as headache, high blood pressure and asthma. Other medical conditions which may be treated by the inventive method include, but are not limited to: pain, movement disorders, epilepsy, cerebrovascular diseases, autoimmune diseases, sleep disorders, autonomic disorders, abnormal metabolic states, disorders of the muscular system, and neuropsychiatric disorders.

Figure 1:
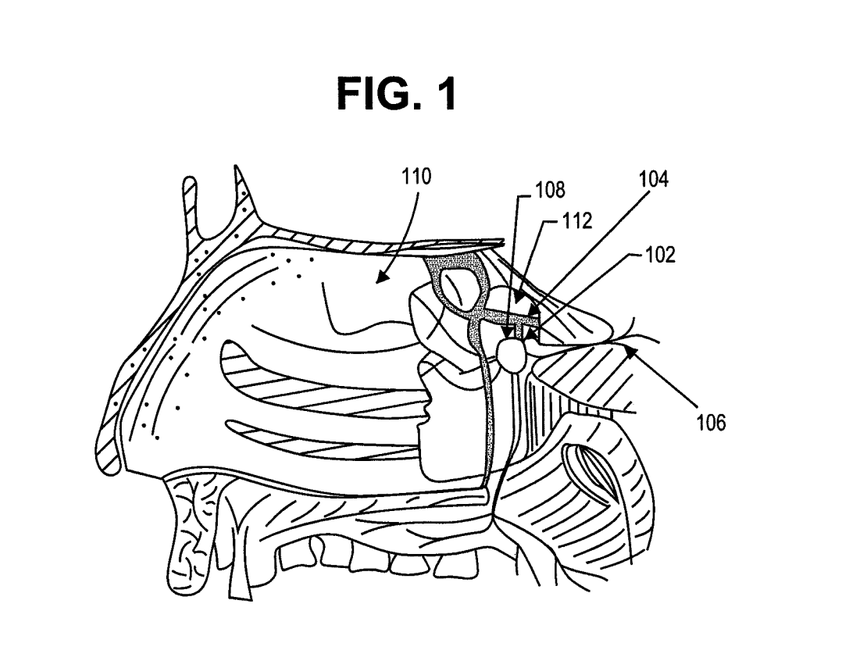
FIG. 1 is an anatomical view of the side of a human head.

FIG. 1 is a schematic illustration of the anatomy the left side of the human head, including the sphenopalatine ganglion 102 ("SPG"; also called the pterygopalatine ganglion), the maxillary nerve 104 ("V₂"), the vidian nerve 106 ("VN"), and the sphenopalatine nerves 108 ("SPN"; also called the pterygopalatine nerves). It should be understood that the anatomy illustrated in FIG. 1 can be found on both sides of the human head. As shown in FIG. 1, SPG 102 is located behind the nasal endothelium at the rear of the nasal cavity 110 in the pterygopalatine fossa 112.

The deep and greater petrosal nerves join together just before entering the pterygoid canal to form the VN 106. The VN is housed within the vidian canal, which is directly posterior to the SPG 102. The VN 106 connects to the SPG 102 and contains parasympathetic fibers which synapse in the SPG 102, sensory fibers which provide sensation to part of the nasal septum, and also sympathetic fibers.

The SPN 108 are sensory nerves that connect the SPG 102 to the maxillary nerve 104. The SPN 108 traverse through the SPG 102 without synapsing and proceed to provide sensation to the palate. The SPN 108 connect the SPG 102 in the pterygopalatine fossa 112 to V2 104.

Figure 2:
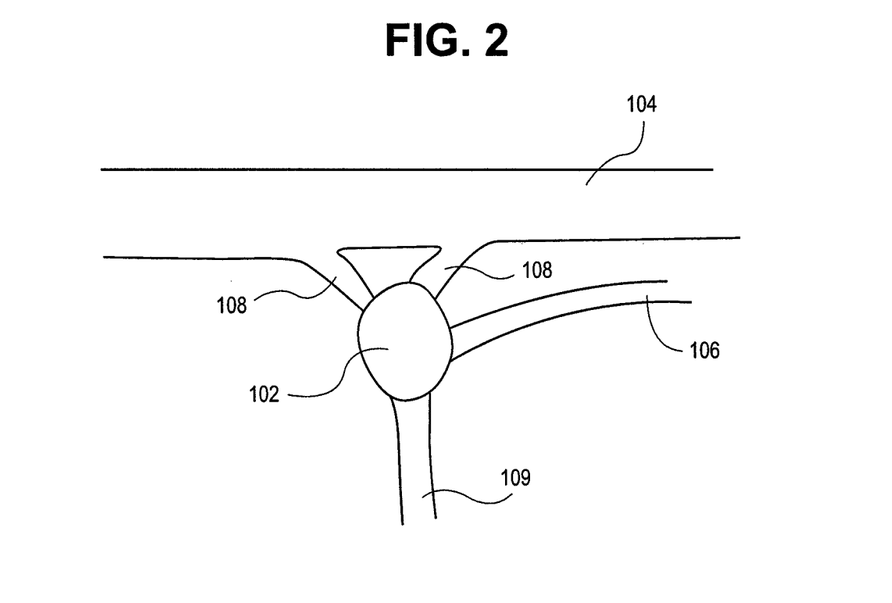
FIG. 2 is a close-up schematic view of the sphenopalatine ganglion and adjacent neural structures.

FIG. 2 illustrates a close-up view of the SPG 102, maxillary nerve 104, VN 106, SPN 108, and palatine nerves 109 shown in FIG. 1. The nerve structures and the relative position and orientation of each nerve can be more easily seen in FIG. 2.

Stimulation of the SPG 102, VN 106, and/or SPN 108 may be used to suppress or prevent undesirable medical conditions by modulating signals passing through the VN 106 and/or the SPG 102. In some embodiments, one or more electrodes are surgically implanted directly on, in or adjacent to the SPG 102, VN 106, SPN 108, and/or other neural structures of a patient.

Figure 3:
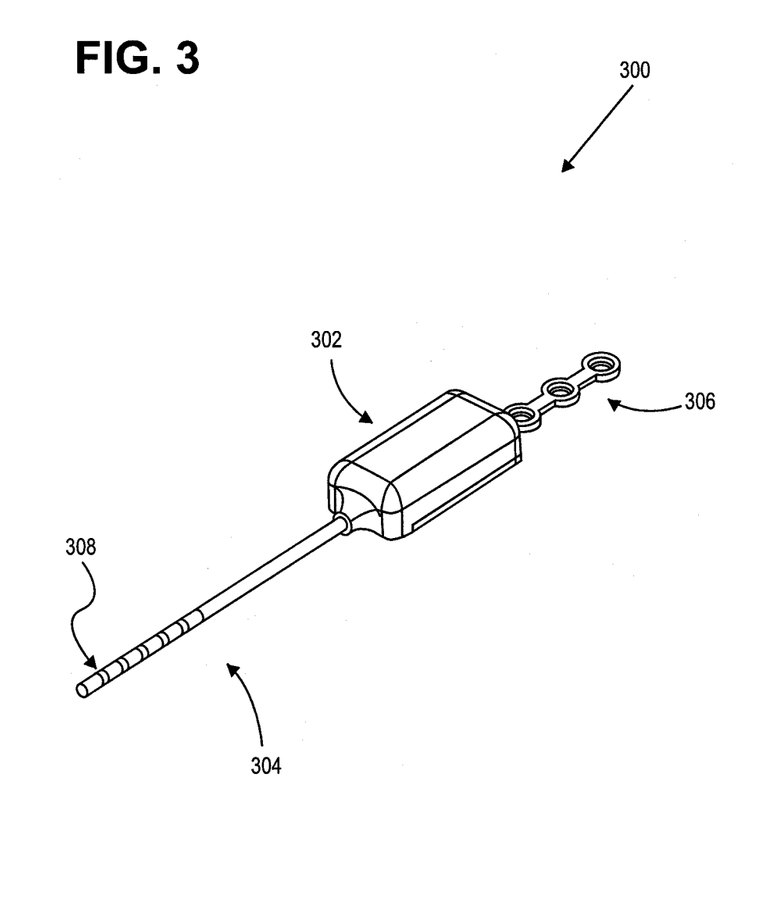
FIG. 3 illustrates an implantable stimulator including a probe assembly having a plurality of electrodes.

FIG. 3 illustrates an implantable stimulator 300 configured to be implanted directly on or adjacent to the SPG, VN, SPN, or similar neural structure. Stimulator 300 can include an electronics enclosure 302, a probe assembly 304, and a fixation portion 306. The stimulator can be anchored or screwed to the desired location in a patient such as by using clinically standard maxillofacial screws through the fixation portion 306, for example. In some embodiments, the stimulator does not include a fixation portion as shown in FIG. 3 and can be secured within a patient by other methods known in the art.

The electronics enclosure 302 can house electronics adapted to produce an electrical stimulation signal, typically a biphasic constant current pulse although other wave forms including low frequency sine-wave signals may be used. The electronics enclosure can also house or be connected to a power source (such as a battery or energy harvester) which can provide the energy source for electrical stimulation. The power source may be a battery implanted in the electronics enclosure or positioned adjacent to the stimulator. In some embodiments, the power source may be implanted at a remote site on the head or body away from the site of the electrical stimulation. In another embodiment, the stimulator can be inductively powered and include the necessary electronics to store programmable stimulation parameters and a bi-directional telemetry to facilitate communication between the implanted stimulator and an external power transmission and communication system. In other embodiments, it may become possible to obtain the energy needed to power the electrode directly from living tissues surrounding the electrode, such as nervous tissues, muscle tissues, bony tissues, or fibrous tissues.

Probe assembly 304 can include at least one electrode 308, which can be activated via the stimulator electronics for producing electrical stimulation. The probe assembly can provide a conduit to deliver electrical stimulation signals between the enclosed electronics and the distal electrodes of the probe to stimulate the anatomical target. The electrodes on the probe assembly may operate in a mono-polar, bipolar, or multi-polar mode. As shown in FIG. 3, the electrode 308 can be a macro-electrode. However, in other embodiments the electrode can be a needle electrode, micro-electrode, electrode cuff, or other similar electrode.

The electrode is preferably controllable to produce stimulating signals which can be varied in voltage, frequency, pulse width, and current. Further, the electrode is also preferably controllable such that the controller may produce both positive and negative current flow from the electrode, stop current flow from the electrode, or change the direction of current flow from the electrode. In some embodiments, the electrode can be configured to monitor an electroneurogram (ENG) of the patient. The controller preferably also has the capacity to produce a variety of stimulation waveforms such as rectangular, triangular and sinusoidal.

FIGS. 4-7 illustrate a method for properly positioning a probe assembly of an electrical stimulator on or adjacent to a target neural structure, such as the SPG. In one embodiment, the probe assembly can be positioned by sensing an ENG of the patient. Correct positioning of the probe can be determined by monitoring the ENG. When the probe assembly comes into contact with the target neural structure, a characteristic ENG can be detected thereby confirming appropriate positioning of the probe. The target neural structure may be identified by detection of a characteristic ENG such as activity, time domain signals, frequency domain signals, amplitude, and patterns such as spikes or bursting. The technique can be used to locate the SPG, the VN, the SPN, the maxillary nerve, or other neural targets.

A variety of methods may be used to surgically implant the electrode on or adjacent to the SPG, the VN, the SPN, or other similar neural structures. In some embodiments, an electrode introducer needle is used to implant the electrode on or proximate to the target neural structure. In one embodiment, an electrode introducer needle can be a 22-gauge needle which is 10 cm long and has a stylet, for example. Other details of inserting an electrode into a patient can be found in U.S. Pat. No. 6,526,318, filed on Jun. 16, 2000, titled "Stimulation method for the sphenopalatine ganglia, sphenopalatine nerve, or vidian nerve for treatment of medical conditions," which is herein incorporated by reference in its entirety.

Since various neural structures can have differing ENG characteristics, a physician or surgeon can observe measured ENG characteristics to determine which neural structure the probe assembly is touching. Thus, in one method, an electrode can be inserted into a patient. The electrode can be positioned on or proximate to a neural structure, and the electrode can detect an ENG signal. Placement of the electrode can be tested by detecting a characteristic ENG. If the characteristic ENG indicates that the electrode is not positioned on the target neural structure, the electrode can be repositioned and the detecting and testing steps can be repeated. If a characteristic ENG is not detected, the electrode can be repositioned and the detecting and testing steps can be repeated. In some embodiments, the physician can observe a characteristic ENG such as time domain or frequency domain signals sensed by the probe assembly to properly position the neurostimulator. In other embodiments, the characteristic ENG can be an amplitude characteristic, a bursting pattern, or a spiking pattern of the detected signal. Monitoring the ENG signal in the frequency domain can be advantageous because it is less affected by impedances and distance from neural targets that can have a dramatic effect on the amplitude of the time domain signal. Alternatively, the ENG signals can be amplified to drive an audio speaker and the physician can listen to the ENG signals to position the probe assembly at the desired target tissue.

Figure 4:
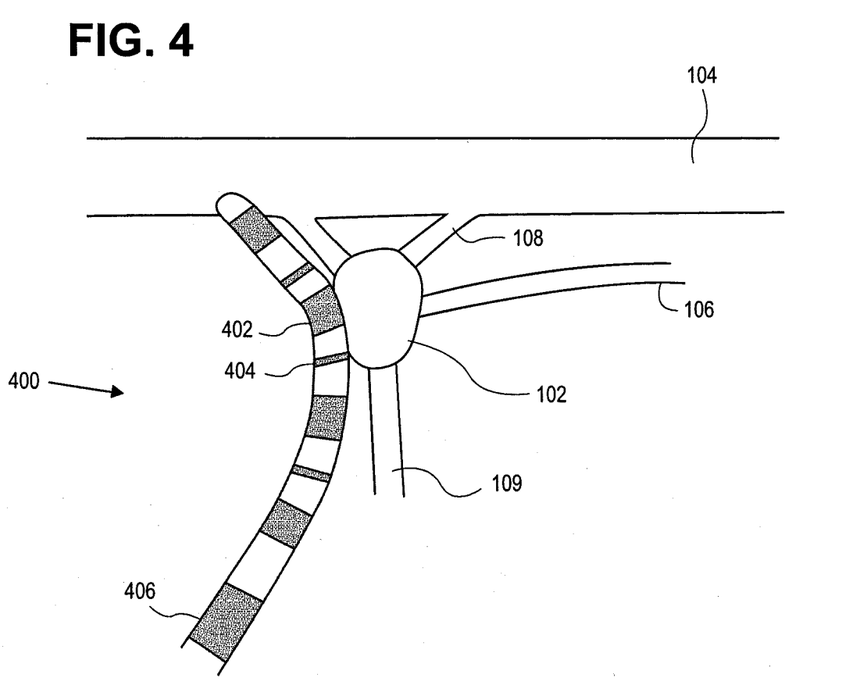
FIG. 4 illustrates an implantable stimulator adjacent to neural structures.

FIG. 4 illustrates a probe assembly adapted to sense an ENG signal from tissue and deliver electrical stimulation to the tissue. In FIG. 4, probe assembly 400 includes macro-electrodes 402 and micro-electrodes 404. The probe assembly can also include an indifferent or return electrode 406, which is preferably positioned a short distance away from the target neural structure to maximize signal amplitude while minimizing extraneous signals such as muscle potentials. In FIG. 4, one macro-electrode is positioned near the maxillary nerve 104 and another macro-electrode is positioned against the SPG. A micro-electrode 404 is also in contact with the SPG. Macro-electrodes are generally preferable for electrical stimulation and micro-electrodes are generally preferable for sensing ENG signals especially during implantation (before any fibrotic tissue develops). Signals recorded from the macro-electrode positioned against the SPG can provide a spatial average of the SPG as well as the surrounding medium, which typically has no signal. Thus, the resulting ENG can be very small when sensed by a macro-electrode. However since the micro-electrode consumes far less spatial area than the macro electrode, ENG signals recorded by the micro-electrode can be considerably larger than the signals recorded by the macro-electrode. Thus, in some embodiments, macro-electrodes can be used to provide electrical stimulation to tissue and micro-electrodes can be used to sense ENG signals from tissue. Both electrode types may be fabricated from known electrode materials such as platinum, platinum-iridium, iridium oxide, titanium nitride, carbon, PEDOT, or other materials, and may be smooth or textured.

Figure 5:
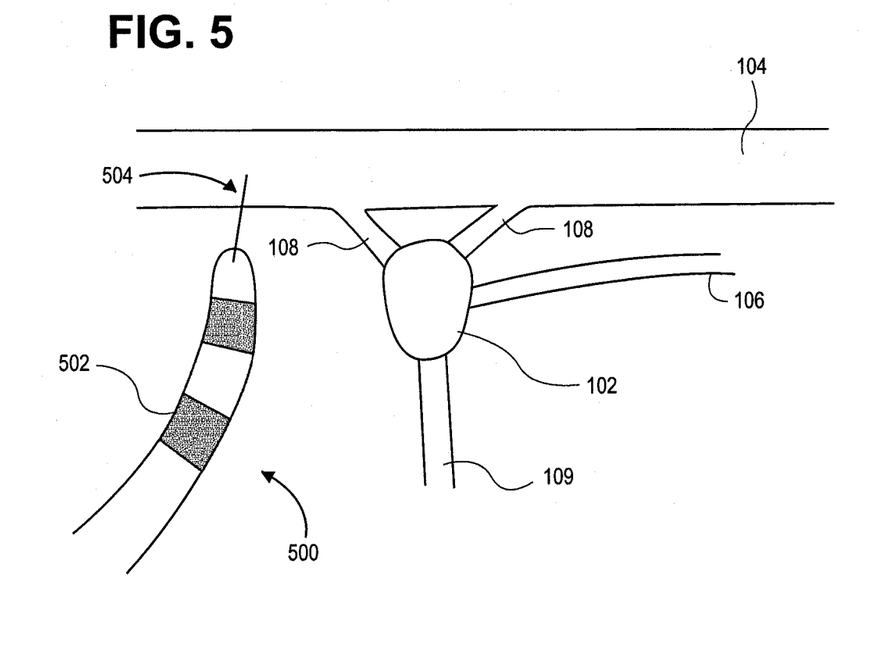
FIG. 5 illustrates an implantable stimulator having a needle electrode in a neural structure.
Figure 6:
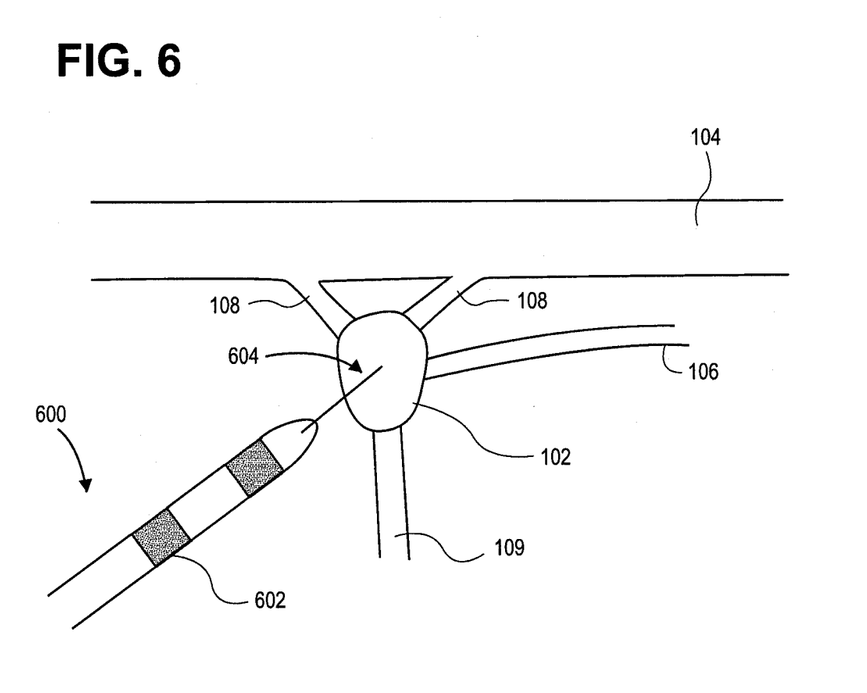
FIG. 6 illustrates an implantable stimulator having a needle electrode in a neural structure.
Figure 7A:
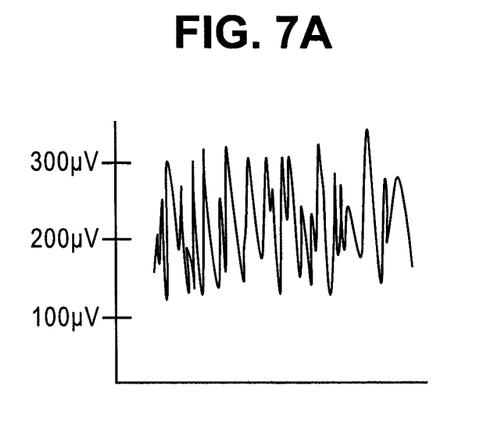
FIGS. 7A-7D illustrate time and frequency domain plots of ENG signals recorded from a neural structure.
Figure 7B:
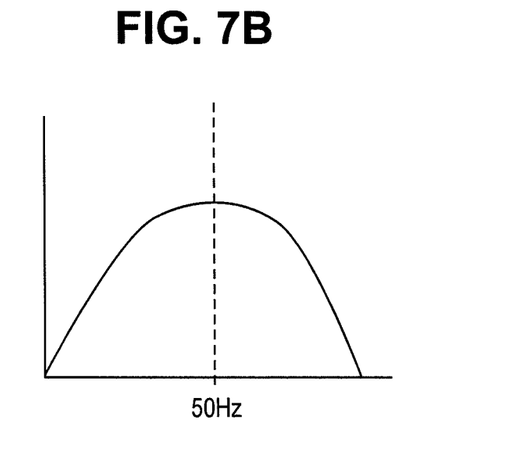

FIGS. 5-6 illustrate another embodiment of a probe assembly adapted to sense an ENG signal from tissue and deliver electrical stimulation to the tissue. The probe assembly can include an integral needle electrode for sensing ENG (such as needle electrodes 500 and 600 in FIGS. 5 and 6, respectively) as well as additional electrodes on the probe assembly for delivering electrical stimulation to neural targets (such as electrodes 502 and 602 in FIGS. 5 and 6, respectively). In FIG. 5, the needle electrode 500 has penetrated the maxillary nerve 104. ENG signals sensed by a needle electrode in the maxillary nerve can produce a large amplitude, high frequency signal, as shown in FIG. 7A. The frequency plot 7B shows the relative strengths of the frequency components of the signal in 7A, having a fairly broad peak centered at approximately 50 Hz or higher. Based on the plots as shown in FIGS. 7A-7B, a physician would know that the needle electrode was positioned in or near the maxillary nerve and not the SPG.

Figure 7C:
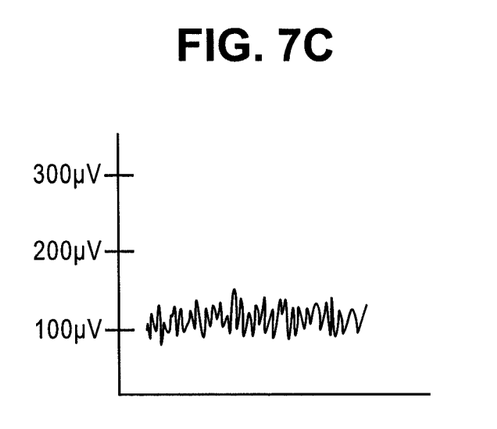
Figure 7D:
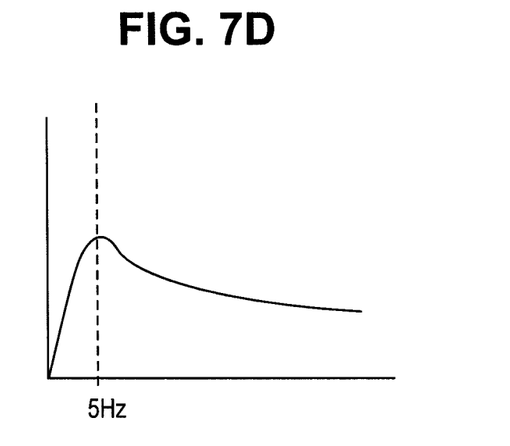

In FIG. 6, the needle electrode 600 has penetrated the SPG 102. ENG signals sensed by the needle electrode in the SPG can produce a comparatively low frequency signal, as shown in FIG. 7C. The main frequency peak for the SPG is around 5 Hz, as shown in FIG. 7D. Based on the plots shown in FIGS. 7C-7D, a physician would know that the needle electrode was positioned in or near the SPG. Thus, a physician can position an implantable neurostimulator at a target neural structure by sensing ENG signals with an electrode and identifying the neurostimulator location based on the sensed ENG signal.

Once the target neural structure is identified, the probe assembly of the stimulator may be placed near the neural structure. In the embodiments of FIGS. 5-6, the probe assembly can be advanced over the needle electrode to bring the other electrodes on the probe assembly (such as electrodes 502 or 602) into contact with the target neural structure.

In an additional embodiment, signal processing of the ENG can be performed to filter and minimize noise and amplify the signal and to process the signal, for example provide a running average value of the envelope of the signal.

It is to be appreciated that, whereas specific embodiments of the present invention are described with respect to a treatment means of at least one electrode and a stimulator that provides electrical current to the SPG or into surrounding neural structures, the scope of the present invention includes other treatment means such as (without limitation) pulsatile electrical stimulation, non-pulsatile and/or low frequency electrical stimulation, medication delivery, change of temperature, application of vibration, ultrasound, pressure, or light or other radiation treatment means that rely on targeting the neural structures.

While embodiments of the present invention are described with respect to a treatment location of cranial nerves such as the SPG, the scope of the present invention includes without limitation other treatment areas in the head, which upon stimulation modulate headache and related disorders, such the vidian nerve, the palatine nerve, the trigeminal nerve or ganglion, the brain, brain stem, spinal cord, peripheral nerves, facial nerves, and neural tracts leading into or away from these areas, as appropriate for the given application.

It is to be appreciated that, whereas described embodiments of the present invention provide a method of determining anatomical location by monitoring the electrical activity of neural structures using an electroneurogram, the scope of the present invention includes other neural activity monitoring methods such as monitoring the electroencephalogram (EEG) or autonomic responses such as pupil dilation/contraction, heart rate, heart rate variability, blood pressure, skin temperature and blood flow.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of positioning an electrode on or proximate to at least one of a patient's sphenopalatine ganglia, sphenopalatine nerves, or vidian nerves, comprising:
    inserting an electrode into the patient;
    detecting an ENG with the electrode;
    testing placement of the electrode by detecting a characteristic ENG; and
    repositioning the electrode if the characteristic ENG is not detected.

2. The method of claim 1 further comprising activating the electrode to apply an electrical signal to at least one of the sphenopalatine ganglia, sphenopalatine nerves, or vidian nerves.

3. The method of claim 1 further comprising repeating the detecting and testing steps.

4. The method of claim 1 wherein the characteristic ENG is a time domain profile.

5. The method of claim 1 wherein the characteristic ENG is a frequency profile.

6. The method of claim 1 wherein the characteristic ENG is an amplitude characteristic.

7. The method of claim 1 wherein the characteristic ENG is a bursting pattern.

8. The method of claim 1 wherein the characteristic ENG is a spikes pattern.

9. The method of claim 1 wherein the electrode is a needle electrode.

10. The method of claim 1 wherein the electrode is a micro-electrode.

11. The method of claim 1 wherein the electrode is a macro-electrode.

* * * * *